United States Patent [19]

Kelly

[11] Patent Number: 5,230,828
[45] Date of Patent: Jul. 27, 1993

[54] NAPHTHALENEDICARBOXYLIC ACID ESTERS

[75] Inventor: Stephen Kelly, Möhlin, Switzerland

[73] Assignee: Hoffmann-La Roche Inc., Nutley, N.J.

[21] Appl. No.: 673,545

[22] Filed: Mar. 22, 1991

[30] Foreign Application Priority Data

Mar. 27, 1990 [CH] Switzerland ............... 1009/90

[51] Int. Cl.$^5$ ............... C09K 19/32; C09K 19/58; C07C 69/76; G02F 1/13
[52] U.S. Cl. ............... 252/299.62; 252/299.2; 560/100; 560/76; 359/103
[58] Field of Search ............... 560/100, 76; 252/299.62, 299.2

[56] References Cited

U.S. PATENT DOCUMENTS 5,061,399 10/1991 Jenner et al. ............... 252/299.62

FOREIGN PATENT DOCUMENTS 213841 3/1987 European Pat. Off. .
64/83050 3/1989 Japan .
2209990 8/1990 Japan .
WO87/05017 8/1987 PCT Int'l Appl. .

Primary Examiner—Robert L. Stoll
Assistant Examiner—Cynthia Harris
Attorney, Agent, or Firm—George M. Gould; William H. Epstein; John J. Schlager

[57] ABSTRACT

Optically active dopants of the formula

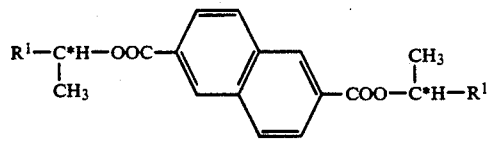

wherein C* denotes a chiral carbon atom and $R^1$ signifies $C_2$–$C_{12}$-alkyl, $C_2$–$C_{12}$-alkenyl, $C_2$–$C_{12}$-alkoxycarbonyl or $C_3$–$C_{12}$-alkenyloxycarbonyl, their manufacture, liquid crystalline mixtures which contain such dopants and their use for optical or electro-optical purposes.

6 Claims, No Drawings

NAPHTHALENEDICARBOXYLIC ACID ESTERS

BACKGROUND OF THE INVENTION

1. Field of the Invention

The present invention is concerned with novel chiral dopants for liquid crystals and their manufacture as well as liquid crystalline mixtures which contain such dopants and their use for optical and electro-optical purposes.

2. Description

Liquid crystal materials for electro-optical indicating devices frequently contain one or more optically active additives for the induction of a chiral structure. For example, for use in indicating devices having a twisted nematic structure a nematic liquid is preferably doped with an optically active additive, e.g. in order to avoid a reversal of the twisting direction (reverse twist) in TN cells (twisted-nematic) or in order to achieve an adequate twisting in cells having an highly twisted nematic structure such as STN cells (super twisted-nematic), SBE cells (super birefringence effect) or OMI cells (optical mode interference). Further, cholestric liquid crystals for phase-change cells can preferably consist of a nematic basic material and one or more optically active dopants and ferroelectric liquid crystals for indicating devices based on chiral tilted smectic phases can preferably consist of a material having a tilted smectic phase and one or more optically active dopants.

The electro-optical characteristics of liquid crystal indicating devices are temperature-dependent, which is especially troublesome in the case of multiplex operation. It is, however, known that this temperature dependence can be compensated at least partially by adding chiral dopants which induce a decreasing pitch with increasing temperature. Such an inverse temperature dependence has been found only for a few compounds. It can, however, also be achieved by using at least 2 chiral dopants which have a different relative temperature dependence and which induce a different twisting direction (U.S. Pat. No. 4,264,148). Of course, this usually requires a relatively high amount of chiral dopants.

Cholesteric liquid crystals reflect light essentially only in a wavelength range for which the wavelength is about the same as the helical pitch. The spectral width of this reflection light can be varied by suitable choice of the liquid crystal. The reflected light is completely circularly polarized. The direction of rotation of the reflected light depends on the direction of rotation of the cholesteric helical structure. The opposite circularly polarized light is transmitted unimpaired. These properties can be employed for the production of optical filters, polarizers, analyzers etc. Further, cholesteric liquid crystals have also variously been used for thermochromic applications and in cosmetic preparations.

Cholesteric liquid crystals for the above applications can preferably consist of a nematic or cholesteric basic material and one or more chiral dopants, which permits a simple adjustment of the desired helical pitch.

In order to produce cholesteric mixtures having a pitch in the range of the wavelength of visible light, the chiral dopants should have a twisting capacity which is as high as possible and should have a good solubility in usual liquid crystal materials. Furthermore, the chiral dopants should have an adequate stability, should have a good compatibility with the mesophase type of the liquid crystal material and should not restrict the mesophase range too strongly. Such properties would also be desirable for chiral dopants for producing the twisted nematic structures referred to earlier, since their amount can be held low in order that the properties of the liquid crystal material are influenced only immaterially.

SUMMARY OF THE INVENTION

The invention is concerned with optically active naphthalene-2,6-dicarboxylic acid esters of the formula

wherein C* denotes a chiral carbon atom and $R^1$ signifies $C_2$–$C_{12}$-alkyl, $C_2$–$C_{12}$-alkenyl, $C_2$–$C_{12}$-alkoxycarbonyl or $C_3$–$C_{12}$-alkenyloxycarbonyl.

The compounds of formula I have a good solubility in usual liquid crystal materials and facilitate a high twisting of the liquid crystal structure. The clearing points of liquid crystals are usually not lowered or are lowered only insignificantly by the addition of compounds of formula I. The compounds of formula I can be manufactured readily, have a relatively low viscosity and have an adequate stability towards electric and magnetic fields. They therefore fulfill the aforementioned requirements in an optimal manner.

DETAILED DESCRIPTION OF THE INVENTION

The invention concerns compounds of the formula

wherein C* is a chiral carbon atom and $R^1$ is $C_2$–$C_{12}$-alkyl, $C_2$–$C_{12}$-alkenyl, $C_2$–$C_{12}$-alkoxycarbonyl or $C_3$–$C_{12}$-alkenyloxycarbonyl, wherein both chiral carbon atoms C* have the S-configuration or the R-configuration.

The compounds of formula I have a good solubility in usual liquid crystal materials and facilitate a high twisting of the liquid crystal structure. The clearing points of liquid crystals are usually not lowered or are lowered only insignificantly by the addition of compounds of formula I. The compounds of formula I can be manufactured readily, have a relatively low viscosity and have an adequate stability towards electric and magnetic fields. They therefore fulfill the aforementioned requirements in an optimal manner.

It will be understood that the chiral carbon atoms in formula I should both have the R-configuration or should both have the S-configuration in order to produce optical activity and a high twisting capacity.

$R^1$ can be straight-chain or branched-chain, and optionally chiral. In general, however, straight-chain residues $R^1$ are preferred.

The term "alkyl" denotes straight or branched alkyl groups of 1 or 12 carbon atoms.

The term "C$_2$-C$_{12}$-alkyl" embraces above straight and branched-chain residues such as ethyl, propyl, butyl, pentyl, hexyl, heptyl, octyl, nonyl, decyl and the like.

The term "C$_2$-C$_{12}$-alkenyl" embraces straight and branched-chain residues such as vinyl, allyl, propenyl, butenyl, pentenyl, hexenyl, heptenyl, octenyl, nonenyl, decenyl and the like.

The term "C$_2$-C$_{12}$-alkoxycarbonyl" embraces straight and branched-chain residues such as methoxycarbonyl, ethoxycarbonyl, propyloxycarbonyl, butyloxycarbonyl, pentyloxycarbonyl, hexyloxycarbonyl, heptyloxycarbonyl, octyloxycarbonyl and the like.

The term "C$_3$-C$_{12}$-alkenyloxycarbonyl" embraces straight and branched-chain residues such as vinyloxycarbonyl, allyloxycarbonyl, propenyloxycarbonyl, butenyloxycarbonyl, pentenyloxycarbonyl, hexenyloxycarbonyl, heptenyloxycarbonyl, octenyloxycarbonyl, 2,6-dimethyl-5-hepten-1-yloxycarbonyl and the like. 2E-Alkenyloxycarbonyl groups and alkenyloxycarbonyl groups having a terminal double bond are generally preferred.

The term "alkoxy", as well as any other groups in the specification containing "alkyl" denotes moieties in which their "alkyl" portions are as defined previously.

Those compounds of formula I in which R$^1$ has a maximum of 7 carbon atoms are especially preferred.

The compounds of formula I can be manufactured in accordance with the invention by esterifying naphthalene-2,6-dicarboxylic acid or a suitable derivative of naphthalene-2,6-dicarboxylic acid with an optically active compound of the formula

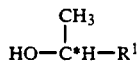

II wherein C* and R$^1$ have the above significances.

The esterification can be effected in a manner known per se. Suitable derivatives of naphthalene-2,6-dicarboxylic acid are, for example, the acid halides, e.g. naphthalene-2,6-dicarboxylic acid chloride. A preferred method comprises reacting a naphthalene-2,6-dicarboxylic acid halide in an inert organic solvent (e.g. an aromatic or saturated, optionally chlorinated hydrocarbon such as benzene, toluene, hexane or carbon tetrachloride) in the presence of an acid-binding agent (e.g. pyridine).

The starting materials are known or are analogues of known compounds.

The invention is also concerned with a liquid crystalline mixture containing a liquid crystalline carrier material and one or more optically active compounds of formula I. Suitable carrier materials are basically all liquid crystal materials which have a twistable liquid crystal phase with an adequate mesophase range. The compounds of formula I are especially suitable as chiral dopants for nematic or cholesteric carrier materials. The liquid crystalline carrier material can be a single compound or a mixture and preferably has a clearing point of at least about 60° C.

The amount of chiral dopant of formula I is determined essentially by its twisting capacity and the desired pitch. The amount of chiral dopant can therefore, depending on the application, vary in a wide range and can be, for example, about 0.1-30 wt. %. For indicating devices based on liquid crystals having a twisted nematic structure a pitch of about 3-40 μm is usually required depending on the type of cell and thickness of cell and therefore a correspondingly smaller amount is sufficient (mainly about 0.1-1 wt. %). On the other hand, for applications which are based on the reflection of visible light by cholesteric layers, pitches of less than 2 μm, for example about 0.4-0.6 μm, are required, which necessitates a correspondingly higher amount of chiral dopant (mainly about 2-20 wt. %). The amount of chiral dopant is mainly about 0.3-3 wt. % for cells having a highly twisted nematic structure.

Suitable liquid crystalline carrier materials are known in large numbers and are commercially available. As a rule, liquid crystalline mixtures containing 2 or more components are preferred as carrier materials. Basically, however, one liquid crystalline compound can be used as the carrier material when it has a sufficiently broad mesophase.

Compounds of the following formulae are especially suitable as components for liquid crystalline carrier materials

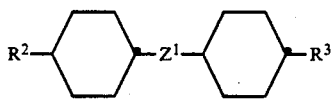

III

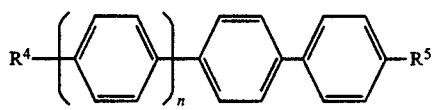

IV

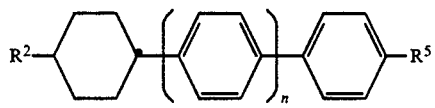

V

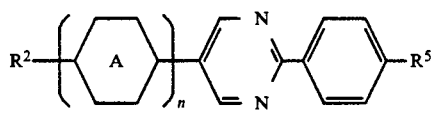

VI

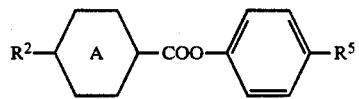

VII

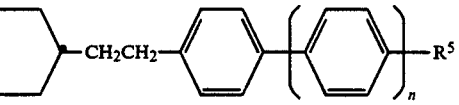

VIII

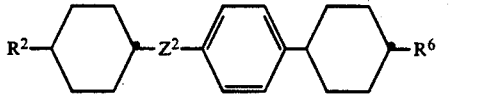

IX

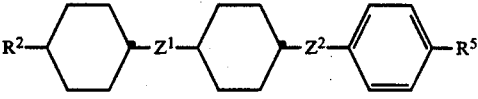

X

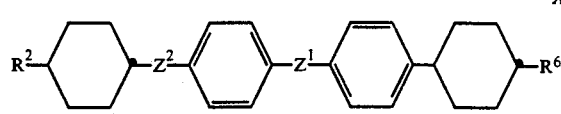

XI wherein $R^2$ and $R^6$ each independently is alkyl or alkenyl; $R^3$ is cyano, alkyl, alkoxy, alkenyl, alkenyloxy, alkoxymethyl or alkenyloxymethyl; $Z^1$ is a single covalent bond or —CH$_2$CH$_2$—; n is the integer 0 or 1; $R^4$ is alkyl, alkoxy, alkenyl or alkenyloxy; $R^5$ is cyano, alkyl, alkoxy, alkenyl or alkenyloxy; ring A is 1,4-phenylene or trans-1,4-cyclohexylene; and $Z^2$ is a single covalent bond, —COO— or —CH$_2$CH$_2$—.

Liquid crystalline mixtures which contain one or more optically active compounds of formula I and one or more compounds from the group of compounds of formulae III–XI are especially preferred.

$R^2$, $R^3$, $R^4$, $R^5$ and $R^6$ each preferably have a maximum of 12 carbon atoms, particularly a maximum of 7 carbon atoms. 1E-Alkenyl, 3E-alkenyl and 4Z-alkenyl are preferred alkenyl groups. 2E-Alkenyloxy and 3Z-alkenyloxy are preferred alkenyloxy groups.

The invention is illustrated in more detail by the following Examples. In connection with liquid crystal phases and phase transitions, C signifies a crystalline phase, N signifies a nematic phase, N* signifies a cholesteric (chiral nematic) phase and I signifies the isotropic phase. The helical pitch is denoted by p and the wavelength of the selectively reflected, circularly polarized light is denoted by $_{max}$. Optical antipodes have in each case "mirror image properties", i.e. the same melting point etc., but lead to an opposite helical direction of rotation and an opposite circular polarization of the reflected light. Unless indicated otherwise, the examples were carried out as written.

EXAMPLE 1

A mixture of 0.4 g of naphthalene-2,6-dicarboxylic acid chloride, 0.5 g of butyl S(+)-lactate, 1 ml of absolute pyridine and 50 ml of absolute toluene was heated overnight under slight reflux and under a nitrogen atmosphere. Thereafter, the reaction mixture was washed in succession with 500 ml of water, 100 ml of dilute hydrochloric acid and again with 500 ml of water, dried over magnesium sulphate, filtered and subsequently concentrated. The residue was purified by chromatography on silica gel with toluene/ethyl acetate (vol. 4:1). Recrystallization from ethanol gave 0.4 g of bis-[(S)-1-(butyloxycarbonyl)ethyl] 2,6-naphthalenecarboxylate with m.p. (C-I) 81° C.

The naphthalene-2,6-dicarboxylic acid chloride used as the starting material was prepared as follows:

A mixture of 1 g of naphthalene-2,6-dicarboxylic acid and 100 ml of toluene was treated with 2 ml of thionyl chloride under a nitrogen atmosphere and subsequently heated under slight reflux overnight. The reaction mixture was concentrated, then treated with 50 ml of absolute toluene and again concentrated. This procedure was repeated twice. Subsequently, the solid residue was sublimed in a bulb tube. This gave 0.8 g of naphthalene-2,6-dicarboxylic acid chloride.

The following compounds can be manufactured in an analogous manner:

Bis-[(S)-1-(methoxycarbonyl)ethyl] 2,6-naphthalenedicarboxylate, m.p. (C-I) 120° C.;
bis-[(S)-1-(ethoxycarbonyl)ethyl] 2,6-naphthalenedicarboxylate, m.p. (C-I) 74° C.;
bis-[(S)-1-(propyloxycarbonyl)ethyl]2,6-naphthalenedicarboxylate, m.p. (C-I) 121° C.;
bis-[(S)-1-(pentyloxycarbonyl)ethyl]2,6-naphthalenedicarboxylate;
bis-[(S)-1-(hexyloxycarbonyl)ethyl] 2,6-naphthalenedicarboxylate;
bis-[(S)-1-(hexenylcarbonyl)ethyl] 2,6-naphthalenedicarboxylate, m.p. (C-I) 70° C.;
bis-[(R)-2-pentyl] 2,6-naphthalenedicarboxylate, m.p. (C-I) 76° C.;
bis-[(R)-2-hexyl] 2,6-naphthalenedicarboxylate, m.p. (C-I) 53° C.;
bis-[(R)-2-heptyl] 2,6-naphthalenedicarboxylate;
bis-[(R)-2-octyl] 2,6-naphthalenedicarboxylate, m.p. (C-I) 4° C.;
bis-[(R)-2-nonyl] 2,6-naphthalenedicarboxylate.

EXAMPLE 2

The following liquid crystal basic mixture BM-1 was used to measure the induced pitch and its temperature dependence in liquid crystal materials.

5.36 wt. % of 4'-ethyl-4-cyanobiphenyl,
3.18 wt. % of 4'-propyl-4-cyanobiphenyl,
6.08 wt. % of 4'-butyl-4-cyanobiphenyl,
6.53 wt. % of 4-(trans-4-propylcyclohexyl)benzonitrile,
14.67 wt. % of 4-(trans-4-pentylcyclohexyl)benzonitrile,
5.21 wt. % of 4-ethyl-1-(trans-4-propylcyclohexyl)benzene,
16.54 wt. % of 4-ethoxy-1-[2-(trans-4-propylcyclohexyl)ethyl]benzene,
5.60 wt. % of 4''-pentyl-4-cyano-p-terphenyl,
5.71 wt. % of 4'-(trans-4-pentylcyclohexyl)-4-cyanobiphenyl,
15.95 wt. % of 1-[2-(trans-4-butylcyclohexyl)ethyl]-4-(trans-4-pentylcyclohexyl)benzene,
4.74 wt. % of 4-[2-(trans-4-butylcyclohexyl)ethyl]-4'-(trans-4-pentylcyclohexyl)biphenyl,
7.59 wt. % of 4-[2-(trans-4-butylcyclohexyl)ethyl]-4'-(trans-4-pentylcyclohexyl)-1,1'-ethylenedibenzene,
2.84 wt. % of trans-4-[2-(trans-4-propylcyclohexyl)ethyl]cyclohexanecarboxylic acid 4-cyanophenyl ester;

m.p. < −30° C., cl.p. (N-I) 90° C.; Δε=8.5, Δn=0.139 and η=22 mPa·s measured at 22° C.

The twisting capacity of the optically active dopant and its temperature dependence is characterized by parameters A, B and C corresponding to the serial progression:

$$\frac{1}{pc} = A + BT_1 + CT_1^2$$

wherein p, c and $T_1$ have the following significances:
$T_1 = T - 22°$ C.
T = temperature in °C.
p = pitch in μm (a positive value signifies a clockwise helical structure and a negative value signifies an anticlockwise helical structure)
c = concentration of the optically active dopant in wt. %.

Mixture M-1

99 wt. % of BM-1,
1 wt. % of bis-[(S)-1-(butyloxycarbonyl)ethyl] 2,6-naphthalenedicarboxylate;
cl.p. (N*-I) 86.7° C.; p (22° C.) = −5.4 μm;
A = −0.1863·μm$^{-1}$·wt. %$^{-1}$,
B = 3.605·10$^{-4}$·μm$^{-1}$·wt. %$^{-1}$·°C.$^{-1}$,
C = 2.838·10$^{-6}$·μm$^{-1}$·wt. %$^{-1}$·°C$^{-2}$.

Mixture M-2

99 wt. % of BM-1, 1 wt. % of bis-[(S)-1-(ethoxycarbonyl)ethyl] 2,6-naphthalenedicarboxylate;
cl.p. (N*-I) 90° C.; p (22° C.) = −4.7 μm;
A = −0.2133·μm$^{-1}$·wt. %$^{-1}$,
B = 4.503·10$^{-4}$·μm$^{-1}$·wt. %$^{-1}$·°C.$^{-1}$,
C = 2.416·10$^{-6}$·μm$^{-1}$·wt. %$^{-1}$·°C.$^{-2}$.

Mixture M-3

99 wt. % of BM-1
1 wt. % of bis-[(R)-2-pentyl] 2,6-naphthalenedicarboxylate;
cl.p. (N*-I) 89.7° C.; p (22° C.) = +24.8 μm;
A = 0.04039·μm$^{-1}$·wt. %$^{-1}$,
B = −0.341·10$^{-4}$·μm$^{-1}$·wt. %$^{-1}$·°C.$^{-1}$,
C = −1.156·10$^{-6}$·μm$^{-1}$·wt. %$^{-1}$·°C.$^{-2}$.

Mixture M-4

99 wt. % of BM-1,
1 wt. % of bis-[(R)-2-hexyl] 2,6-naphthalenedicarboxylate;
cl.p. (N*-I) 89,8° C.; p (22° C.) = +11.7 μm;
A = 0.0853·μm$^{-1}$·wt. %$^{-1}$,
B = −2.711·10$^{-4}$·μm$^{-1}$·wt. %$^{-1}$·°C.$^{-1}$,
C = −1.710·10$^{-6}$·μm$^{-1}$·wt. %$^{-1}$·°C.$^{-2}$.

Mixture M-5

99 wt. % of BM-1,
1 wt. % of bis-[(R)-2-octyl] 2,6-naphthalenedicarboxylate;
cl.p. (N*-I) 88.6° C.; p (22° C.) = +9.4 μm;
A = 0.1059·μm$^{-1}$·wt. %$^{-1}$,
B = −4.245·10$^{-4}$·μm$^{-1}$·wt. %$^{-1}$·°C.$^{-1}$,
C = −3.163·10$^{-6}$·μm$^{-1}$·wt. %$^{-1}$·°C.$^{-2}$.

I claim:

1. A compound of the formula

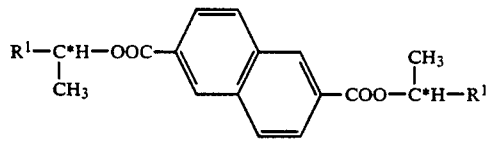

I wherein C* is a chiral carbon atom, and $R^1$ is $C_2$-$C_{12}$-straight chain alkyl, $C_2$-$C_{12}$-alkenyl, $C_2$-$C_{12}$-alkoxycarbonyl or $C_3$-$C_{12}$-alkenyloxycarbonyl, in which both chiral carbon atoms C* have the S-configuration or the R-configuration.

2. The compound according to claim 1, wherein $R^1$ has a maximum of 7 carbon atoms.

3. A liquid crystalline mixture comprising:
a) a liquid crystalline carrier material; and
b) at least one compound of the formula:

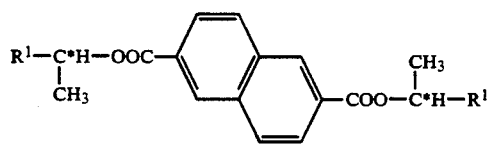

I wherein C* is a chiral carbon atom, and $R^1$ is $C_2$-$C_{12}$-straight chain alkyl, $C_2$-$C_{12}$-alkenyl, $C_2$-$C_{12}$-alkoxycarbonyl or $C_3$-$C_{12}$-alkenyloxycarbonyl, in which both chiral carbon atoms C* have the S-configuration or the R-configuration.

4. The liquid crystalline mixture according to claim 3, wherein the amount of compound I is about 0.1 to about 30 wt. percent of the mixture.

5. The liquid crystalline mixture according to claim 3, further comprising at least one compound selected from the group of compound of the formulae

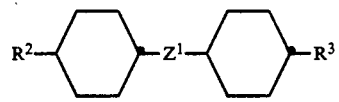

III

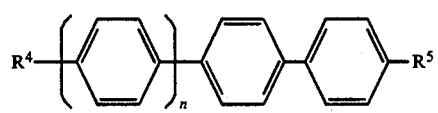

IV

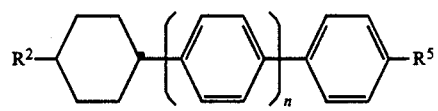

V

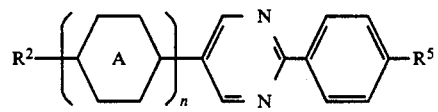

VI

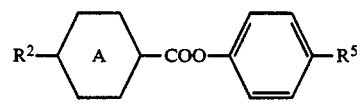

VII

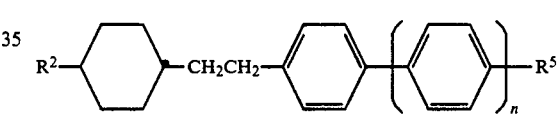

VIII

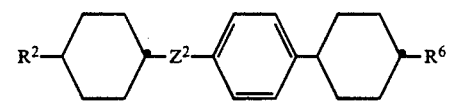

IX

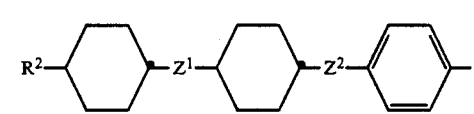

X

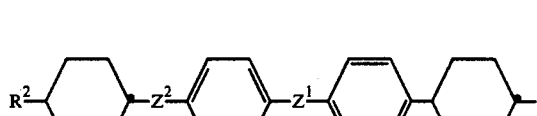

XI wherein $R^2$ and $R^6$ each independently is alkyl or alkenyl; $R^3$ is cyano, alkyl, alkoxy, alkenyl, alkenyloxy, alkoxymethyl or alkenyloxymethyl; $Z^1$ is a single covalent bond or —CH$_2$CH$_2$—; n is the integer 0 or 1; $R^4$ is alkyl, alkoxy, alkenyl or alkenyloxy; $R^5$ is cyano, alkyl, alkoxy, alkenyl or alkenyloxy; ring A is 1,4-phenylene or trans-1,4-cyclo-hexylene; and $Z^2$ is a single covalent bond, —COO— or —CH$_2$CH$_2$— $R^2$, $R^3$, $R^4$, $R^5$ and $R^6$ each having a maximum of 12 carbon atoms.

6. An electro-optical cell comprising:
a) two-plate means;
b) a liquid crystal mixture disposed between the plate means and which includes a compound of the formula

wherein C* is a chiral carbon atom, and $R^1$ is $C_2$-$C_{12}$-straight chain alkyl, $C_2$-$C_{12}$-alkenyl, $C_2$-$C_{12}$-alkoxycarbonyl or $C_3$-$C_{12}$-alkenyloxycarbonyl, in which both chiral carbon atoms C* have the S-configuration or the R-configuration; and
c) means for applying an electrical potential to said plate means.
* * * * *